US008617200B2

(12) United States Patent
McIntosh et al.

(10) Patent No.: US 8,617,200 B2
(45) Date of Patent: Dec. 31, 2013

(54) MULTI-LAYER FILTRATION DEVICE

(75) Inventors: Charles L. McIntosh, Silver Spring, MD (US); Shyam Kuppurathanam, Bloomington, IN (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 49 days.

(21) Appl. No.: 13/211,409

(22) Filed: Aug. 17, 2011

(65) Prior Publication Data

US 2013/0046330 A1 Feb. 21, 2013

(51) Int. Cl.
*A61M 29/00* (2006.01)
(52) U.S. Cl.
USPC ........................................................ 606/200
(58) Field of Classification Search
USPC ........................................................ 606/200
See application file for complete search history.

(56) References Cited

U.S. PATENT DOCUMENTS

| 3,765,536 | A | 10/1973 | Rosenberg | |
|---|---|---|---|---|
| 3,765,537 | A | 10/1973 | Rosenberg | |
| 4,033,881 | A | 7/1977 | Pall | |
| 4,073,732 | A | 2/1978 | Lauer et al. | |
| 4,303,530 | A | 12/1981 | Shah et al. | |
| 2006/0253148 | A1* | 11/2006 | Leone et al. | 606/200 |
| 2007/0088383 | A1* | 4/2007 | Pal et al. | 606/200 |
| 2008/0234722 | A1* | 9/2008 | Bonnette et al. | 606/200 |
| 2010/0185230 | A1* | 7/2010 | Horan et al. | 606/200 |
| 2010/0268264 | A1* | 10/2010 | Bonnette et al. | 606/200 |

* cited by examiner

*Primary Examiner* — Melanie Tyson
(74) *Attorney, Agent, or Firm* — Brinks Gilson & Lione

(57) ABSTRACT

A filter device assembly and a method of using such a device to capture and remove embolic material from a body lumen or blood vessel are provided. The filter device assembly generally includes a structure having a collapsed state and an expanded state with first, second, and optionally N additional filter members circumferentially attached thereto. Each filter member forms an annulus chamber with the first filter member having porosity $P_1$; the second filter member circumferentially having porosity $P_2$; and the N additional filter members each having porosity $[P_3 \ldots P_{(2+N)}]$. The magnitude of the porosity for the first, second, and N additional filter members follows the relationship $P_1 > [P_3 > \ldots > P_{(2+N)}] > P_2$. The first, second, and N additional filter portions are configured in the expanded state to allow blood to flow there through and to capture emboli in the annulus chambers.

10 Claims, 4 Drawing Sheets

MULTI-LAYER FILTRATION DEVICE

FIELD

This disclosure relates generally to medical devices. More specifically, this disclosure relates to a filter device assembly and a method of using such a device to capture and remove embolic material from a body lumen or vessel.

BACKGROUND

Since the kidneys filter or remove waste products and excess fluids from the blood, approximately one-third of the blood delivered from the heart flows through the kidneys. This flow of blood also allows the kidneys to play a major role in regulating the blood pressure in a person. When the build-up of plaque (atherosclerosis), as well as other abnormalities that may occur in the renal artery, cause enough narrowing or blockage of the artery such that the supply of blood to the kidney is reduced, the risk of kidney damage becomes very high. If this condition, i.e., renal artery stenosis, is left untreated it can lead to high blood pressure, reduced functioning of the kidneys, and/or even kidney failure.

A standard procedure used in the treatment of endovascular diseases and abnormalities is the placement of medical devices, such as embolic coils, stents, and dilation balloons, among others, at a desired or targeted site within a patient. The delivery of such a medical device has typically been accomplished by a variety of means, including the use of a catheter through which the device travels for deployment to the targeted site. These medical devices usually have a contracted shape that allows them to pass through the lumen of the catheter and an expanded shape for engagement with the body vessel that occurs after being deployed at the targeted site.

A renal stent is an example of such a medical device. The stent acts as a scaffold, by keeping the artery stretched open and maintaining adequate blood flow through the vessel. However, because renal artery stents are exposed to the flow of blood, they may facilitate the formation of clots until the stent becomes covered with tissue from the body. Various medications are usually given to the patient at this time to prevent the occurrence of thrombosis, i.e., the formation of a blood clot.

In order to increase the safety of using stents and other devices in the vasculature of a patient, embolic protection devices have been developed as a means to capture blood clots and other embolic particles that may become dislodged from a stenosis or the treatment thereof. Such devices may be deployed within a vessel at a site distal, e.g., downstream, to the stenosis before the treatment takes place. In a deployed configuration, the embolic protection device is intended to act as a filter that allows blood to pass through, but traps any embolic particles, such as atherosclenotic plaque or a thrombus, attempting to flow therewith.

Multiple issues exist with the design, manufacturing, and use of existing filter devices. Among these issues is the desirability under certain circumstances to deploy the filter device from the proximal side of the stenosed region. Therefore, the profile of the filtering device should be smaller than the opening through the stenosed region. Another issue, among many, resides in the filter portion being susceptible to becoming clogged or occluded during treatment, thereby, reducing the blood flow through the blood vessel. Accordingly, there is a continual desire to provide improved devices and methods for capturing emboli within a blood vessel. A filter device that provides distal protection during a procedure that has the potential to produce emboli without substantially restricting blood flow through the vessel would be beneficial.

SUMMARY

In satisfying the above need, as well as overcoming the enumerated drawbacks and other limitations of the related art, the present disclosure generally provides a filter device assembly for capturing embolic particles in a blood vessel. The device comprises a structure that has a predetermined shape with a distal portion, proximal portion, and optionally a middle portion. The structure is configured to move between an expanded state for engagement with the blood vessel and a collapsed state for delivery and retrieval. The structure of the filter device in its expanded state has a substantially cylindrical shape.

The filter device assembly further includes a first filter member, a second filter member, and optionally N additional filter members circumferentially attached to the structure with each filter member forming an annulus chamber. The first filter member exhibits porosity, $P_1$, while the second and filter member exhibits porosity, $P_2$. The optional N additional filter members when present each exhibit a porosity, $[P_3 \ldots P_{(2+N)}]$. The porosity associated with each filter member follows the order $P_1 > [P_3 > \ldots > P_{(2+N)}] > P_2$. The first, second, and N additional filter members are configured in the expanded state to allow blood to flow there through and to capture emboli in the annulus chambers.

According to one aspect of the present disclosure, the porosity $P_1$ is at least about 150 micrometers and the porosity $P_2$ is equal to or less than about 50 micrometers. The porosity of each additional filter member, $[P_3 \ldots P_{(2+N)}]$, is greater than about 50 micrometers and less than about 150 micrometers.

According to another aspect of the present disclosure a method for providing embolic protection during the treatment of a stenosis, occlusion, lesion, or other defect in a body vessel is provided. This method generally comprises the steps of introducing a catheter into the body vessel and locating the end of said catheter proximate to a target site. A filter device assembly is then placed into the catheter. This filter device assembly has the configuration and design as described herein. The filter device is moved through the catheter and deployed to the targeted site in a collapsed state. The targeted site is generally downstream or past the stenosis, occlusion, lesion, or other defect in the body vessel. Once deployed in the body vessel, the filter device is allowed to move from its collapsed state to an expanded state. After the filter device assembly has reached its expanded state, the stenosis, occlusion, lesion, or other defect in the body vessel may be treated. Such treatment may include the deployment of a stent or other medical device, chemical dissolution, or mechanical thrombolysis, among others. The method may also comprise the step of withdrawing the catheter from the body vessel.

During the use of the filter device assembly, the first filter portion allows emboli having a diameter larger than porosity, $P_1$, to be captured and emboli having a diameter smaller than porosity, $P_1$, to pass there through along with the flow of blood to the adjacent filter portion. Similarly, the second filter portion allows emboli having a diameter larger than porosity, $P_2$, to be captured and emboli having a diameter smaller than the porosity, $P_2$, to pass through along with the flow of blood. Each of the N additional filter portions allows emboli having a diameter larger than the corresponding porosity, $[P_3 \ldots P_{(2+N)}]$, to be captured and emboli having a diameter smaller than the porosity, $[P_3 \ldots P_{(2+N)}]$, to pass through along with the flow of blood to the adjacent filter portion.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 1B is a close-up view of the center rod coupling the first and second sections together in the multi-layer filter device of FIG. 1A;

DETAILED DESCRIPTION

Figure 1A:
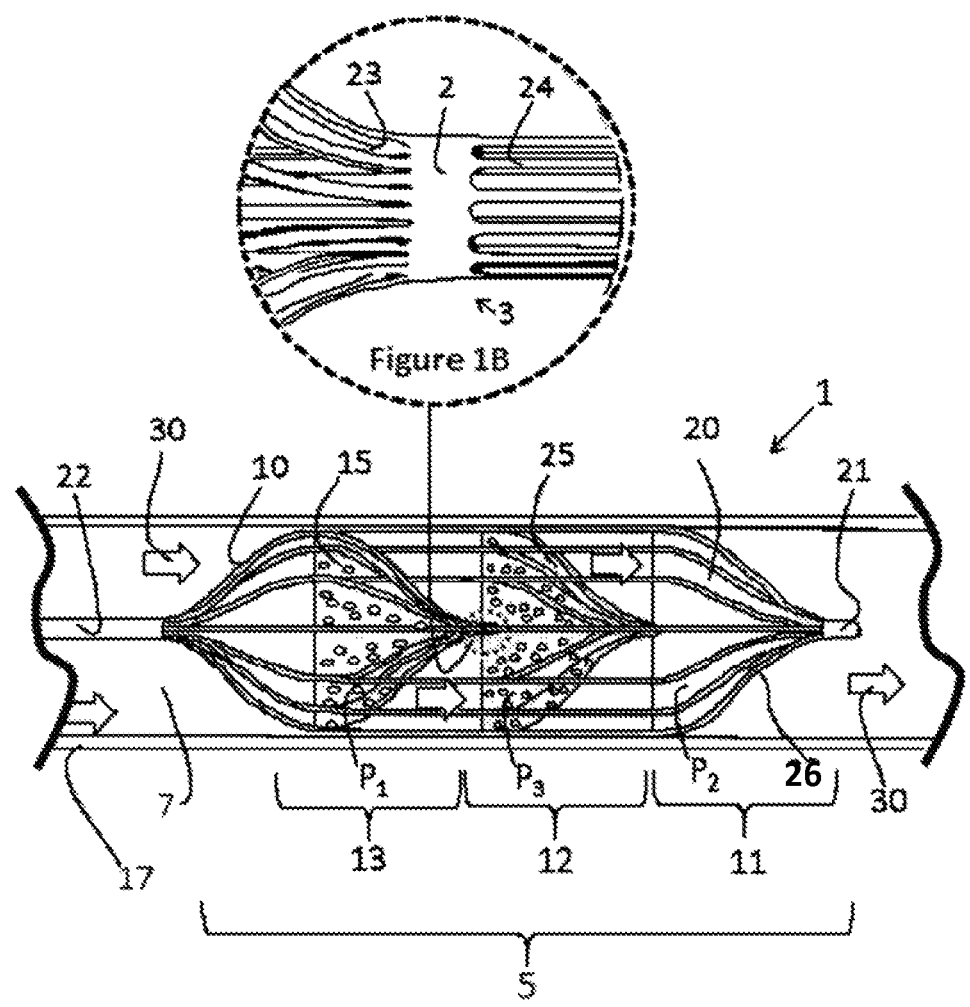
FIG. 1A is a cross-sectional, longitudinal view of a body vessel showing a perspective view of a multi-layer filter device assembly deployed according to one aspect of the present disclosure.

The following description is merely exemplary in nature and is in no way intended to limit the present disclosure or its application or uses. It should be understood that throughout the description and drawings, corresponding reference numerals indicate like or corresponding parts and features.

The present disclosure generally provides a filter device assembly and a method of using such a device to capture and remove embolic material from a body lumen or vessel. As a result, the filter device assembly of the present disclosure may be used to improve the circulation of blood through the body lumen and to reduce the chance of clot or atherosclerotic material related issues, such as embolization at the anterior end of the kidney or with other organs. Although the filter device assembly is depicted in the Figures and described herein to include three filter members, one skilled in the art will understand that the filter device assembly may include any desired number of filter members (e.g., 2, 3, 4, 5, etc.) without exceeding the scope of the present disclosure; provided that the number of filter members is at least two filter members. The desired number of filter members present in the filter device assembly is predetermined by the intended use or medical application for the device assembly.

Referring to FIG. 1A, the filter device assembly 1 as deployed in a body vessel 5 according to one aspect of the present disclosure, comprises a structure 5 having a frame 10 with a predetermined shape; the frame includes a distal 11 portion, a proximal 13 portion, and an optional middle 12 portion. In this example, the filter device assembly 1 is positioned to capture embolic material or thrombi carried by the blood flowing 30 through the artery or body vessel 7 with filter members 15, 20, 25 being fully deployed adjacent to the vessel wall 17. The proximal end of the structure 5 may be coupled to a guide wire 22 or include a hook or other means which can be used to couple to a guide wire 22. The distal end of the structure 5 is preferably open through the use of a hollow hub 21 to allow the passage of a guide wire. The overall structure 5 is configured to move between an expanded state for engagement of the frame 10 with the wall 17 of the body vessel 7 and a collapsed state for delivery and retrieval. A part of the frame 10 may also act as struts 26 that provide support for each filter member 15, 20, 25 in the assembly's 1 expanded state.

The distal 11, optional middle 12, and proximal 13 portions of the filter device assembly 1 may be coupled through any means known to one skilled in the art. One example of coupling the proximal portion 13 to distal portion 11, or to the middle portion 12 and the middle portion 12 to the distal portion 11 when the optional middle portion 12 is present, includes the use of a shaft 3. Referring now to FIG. 1B, the shaft 3 may be hollow or solid and contain a solid, unperforated center section 2 along with proximal 23 and distal 24 perforated sections. The proximal perforated section 23 may be used as struts for supporting the filter members 15, 20, 25 when they are in the expanded state.

Referring once again to FIG. 1A, a first filter member 15 has a proximal part and a distal part, the proximal part is circumferentially attached to the proximal portion 13 of the frame 10 with the distal part of the filter member 15 being coupled to a shaft 3. Similarly, a second filter member 20 has proximal part and distal part, the proximal part is circumferentially attached to the distal portion 11 of the frame 10. The distal part of the second filter member 20 being coupled to the end hub 21. The first filter member 15 forms a first annulus chamber within the device 1 having a first porosity level, $P_1$. The second filter member 20 forms a second annulus chamber within the device 1 having a second porosity level, $P_2$. The filter portions 15, 20, 25 are configured in the expanded state to allow blood to flow 30 there through and to capture emboli in the annulus chambers. The magnitude of the porosity for the first and second filter members follows the relationship $P_1 > P_2$.

The filter device assembly 1 may further comprise N additional filter members, wherein N is an integer greater than or equal to one. Each of the N additional filter members has a proximal part and a distal part, the proximal part circumferentially attached to the middle portion of the frame 10; the distal part closed such that each N additional filter member forms an annulus chamber having a porosity $[P_3 > \ldots > P_{(2+N)}]$. As shown in FIG. 1A, when N=1, a third filter member 25 is present in the filter device assembly 1 forming a third annulus chamber within the device having a porosity level, $P_3$. The magnitude of the porosity for each of the N additional filter members follows the relationship $P_1 > [P_3 > \ldots > P_{(2+N)}] > P_2$. The distal part of each additional filter member may be coupled to the shaft 3.

The porosity of each filter member 15, 20, 25 is given by the relationship $P_1 > [P_3 > \ldots > P_{(2+N)}] > P_2$. According to one aspect of the present disclosure, porosity $P_1$ is at least about 150 micrometers, while porosity $P_2$ is equal to or less than about 50 micrometers. The porosity, $[P_3 \ldots P_{(2+N)}]$, of each additional filter member may be any value that is between $P_1$ and $P_2$. In other words, the porosity $[P_3 \ldots P_{(2+N)}]$ may range between about 50 to about 150 micrometers. In the specific example described in FIG. 1A, a third filter member 25 having a porosity of about 100 micrometers is preferred. According to another aspect of the present disclosure, the porosity $P_2$ should be larger than about 7.5 micrometers in order not to restrict the flow of red and/or white blood cells through the filter device 1.

The number of filter members present in the filter device assembly 1 is predetermined depending upon the expected or intended application or use for the device assembly 1. For example, a filter device assembly 1 having three filter members is preferable for use in the renal artery. Similarly, a filter device assembly 1 having two filter chambers may find use in arteries below the knee, while a device assembly with four or five filter members may find use in other arteries, such as in carotid, superficial femoral, or iliac systems.

Figure 1C:
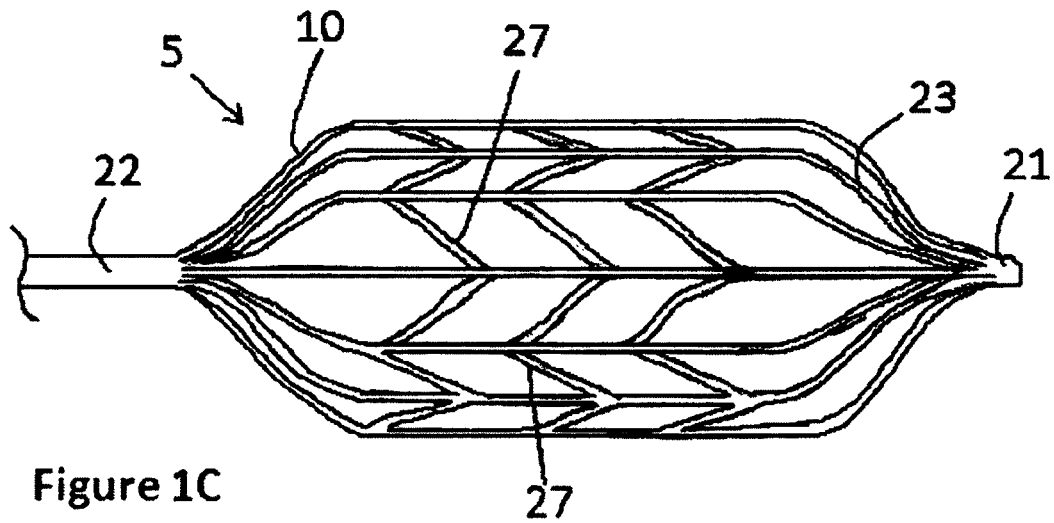
FIG. 1C is a perspective view of the frame surrounding the multi-layer filter device according to another aspect of the present disclosure.

Still referring to FIG. 1A, according to another aspect of the present disclosure, the structure 5 may be configured to provide the body of the filter device assembly 1 with a substantially cylindrical shape in its expanded state. The length of the filter device assembly 1 may vary depending upon the intended application. For example, when used in the renal artery, the length of the filter device assembly is preferably on the order of about 1.5 centimeters. In the expanded state, the shape of the filter device assembly 1 will define an interior volume that provides an entrapment region for capturing and holding embolic material. The spacing within the frame 10 of the structure 5 can be predetermined and configured for use in a given application. Referring now to FIG. 1C, various parts of the frame 10 may be coupled through the use of support wires 27 angled in a predetermined manner to provide the strength and support desired for the structure 5 when in either the collapsed or expanded states. The frame 10 may include struts 23 and other support media arranged in a manner that creates very little resistance to blood flow through the body lumen or vessel. The filter device assembly 1 is preferably configured to be collapsible into a smaller cross-sectional profile for facilitating its delivery to and retrieval from the targeted treatment site. The filter device assembly 1 in its expanded state interacts with the inner walls of the body lumen or vessel in order to secure the device in place and ensure that blood flows through the interior volume of the device 1.

The structure 5 of the filter device assembly 1 may comprise any metal, metal alloy, polymeric material, and/or combination thereof known to one skilled-in-the-art. According to one aspect of the present disclosure, the structure 5 of the filter device assembly 1 may comprise a superelastic material, stainless steel wire, Nitinol, cobalt-chromium-nickel-molybdenum-iron alloy, or cobalt chrome-alloy or any other material suitable for use in a filter device that allows for the transitioning between an expanded state and a collapsed state, as well as extended durability and flexibility. According to another aspect of this disclosure, at least a portion of the filter device assembly 1 may optionally have one or more surface treatments applied thereto, including but not limited to coatings, machining, texturing, electropolishing, media blasting, and chemical etching.

The filter material used in the first 15, second 20, third 25 members, and any other additional filter members may be formed from any suitable material known to one skilled-in-the-art to be used in capturing or trapping embolic particles from a flowing blood stream. The selected material may be independently selected for use in the first 15, second 20, third 25, and other additional filter members. The material selected for use with each member will exhibit the porosity level desired for that member. In one embodiment, the filter material may be made at least partially of a non-woven material, knits, braids, or a textile composite, including, but not limited to, a woven fabric, a molded polymer, a polymer film, or a combination thereof. Such fabrics and polymers may include but not be limited to nylon; poly(tetrafluoroethylene), such as Teflon® (DuPont de Nemours); polyethylene, such as Dyneema® (DSM Dyneema), polyester, such as Dacron® (Invista, Koch Industries), and mixtures or combinations thereof. The filter material may also include a biological graft material, such as small intestinal submucosa (SIS) or another extracellular material (ECM). The graft materials may be cross-linked for stability if desired.

Figure 2:
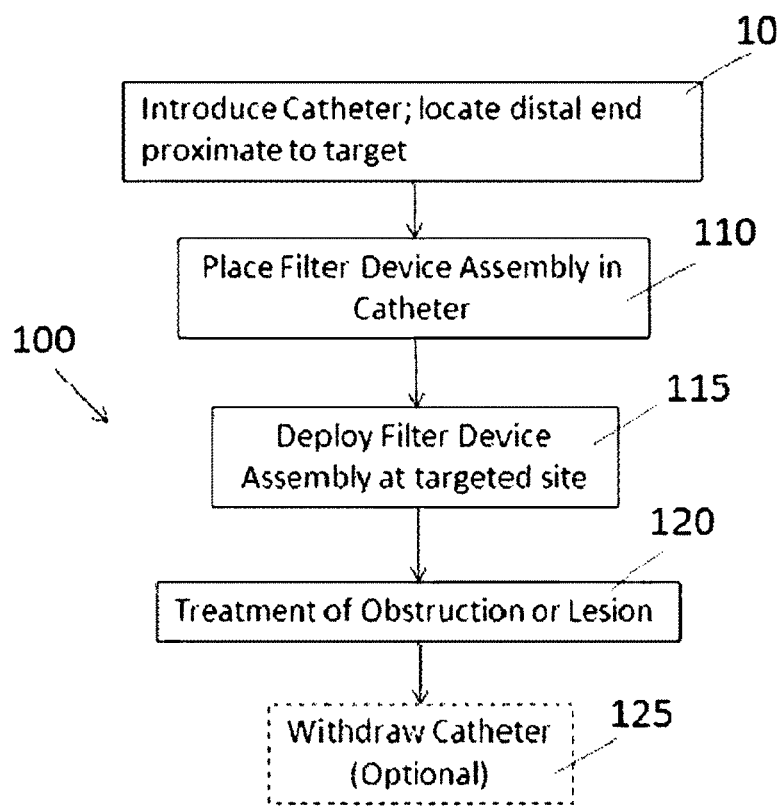
FIG. 2 is a schematic representation of a method of deploying a filter device assembly into a vasculature of a patient; the filter device assembly being made according to the teachings of the present disclosure.

Another objective of the present disclosure is to provide a method 100 of using the filter device assembly 1 described herein at a targeted site in the vasculature 5 of a patient. FIG. 2 depicts an example of a method 100 that uses the filter device assembly 1 described herein. This method 100 generally comprises introducing 105 a catheter into the body vessel of a patient and positioning the distal end of said catheter at a desired or targeted site. The aforementioned filter device assembly 1 is then placed 110 into the catheter in a collapsed state. When desirable, the filter device assembly 1 may be attached to a wire guide and encased within a sheath, and then loaded into the catheter for delivery to the targeted site. A pusher element or another means known to one skilled-in-the-art is then used to move the filter device assembly 1 through the catheter. Upon exiting the catheter, the filter device assembly 1 is deployed 115 at the targeted site and allowed to transition to its expanded state.

The stenosis, occlusion, lesion, or other defect in the body vessel can then be treated 120. Such treatment may include the deployment of a stent, a balloon, or other medical device; chemical dissolution; or mechanical thrombolysis, among others. After performing the necessary or desired treatment, the catheter may be optionally withdrawn 125. In order to further enhance the dissolution of embolic material, one or more thrombolytic drugs or therapeutic agents may be used in addition to the filter device assembly 1. The various components of the filter device assembly 1, or more likely, the stent or other medical device used in conjunction with the filter device assembly may, when desirable, be coated with one or more of such drugs. The therapeutic agents may include, but not be limited to, antiproliferative agents, anti-inflammatory agents, and antiplatelet agents, among others.

The delivery catheter used to deliver the filter device assembly 1 may be made of any material known to one skilled-in-the-art. Such material may include but not be limited a polyimide, polyether amide, nylon, polytetrafluoroethylene (PTFE), polyetheretherketone (PEEK), and mixtures or copolymers thereof. In its basic form, the catheter is a hollow elongated tube sized to receive the medical device assembly 1. The length of the delivery catheter may be any length necessary or desired to deploy the filter device assembly 1 at the targeted site in the vasculature of a patient.

Figure 3A:
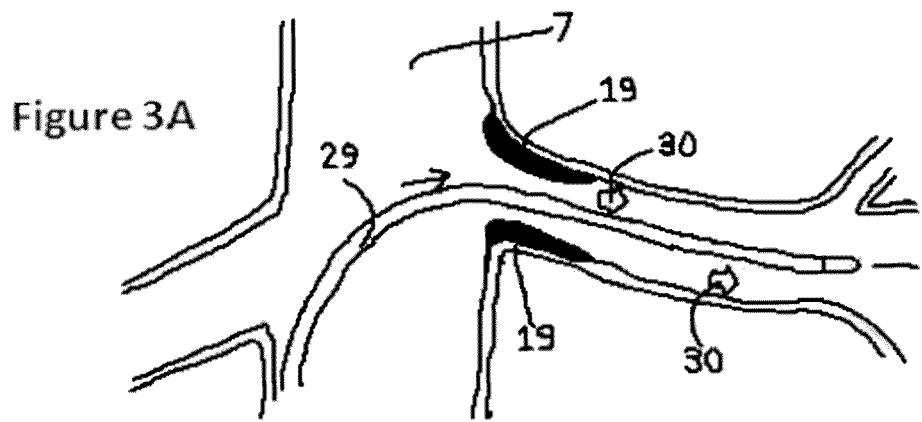
FIG. 3A is a cross-sectional, longitudinal view of a body vessel in which a catheter is positioned downstream from an obstruction according to one aspect of the present disclosure.

Referring now to FIGS. 3A-3F, the deployment and retrieval of the filter device assembly 1 in a body lumen or vessel 7 of a patient is shown. In FIG. 3A the filter device assembly 1 is being delivered into a body lumen or blood vessel 7 by a delivery tube 29 percutaneously through the vasculature (not shown) of a patient. In this case, the filter device assembly 1 is inserted through the proximal end of the delivery tube 29 for delivery to a targeted site in the patient, which is downstream from the obstruction 19 or the region of the vessel 7 to be treated (e.g., lesion, etc.) with respect to the direction of blood flow 30.

Figure 3B:
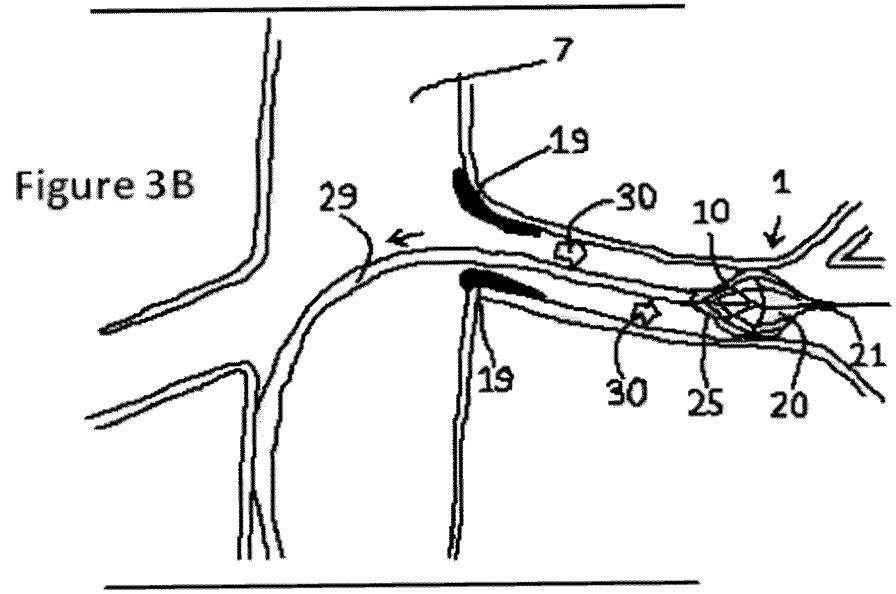
FIG. 3B is a cross-sectional, longitudinal view of the body vessel of FIG. 3A in which the filter device assembly is being deployed in its collapsed state with subsequent transitioning to its expanded state.
Figure 3C:
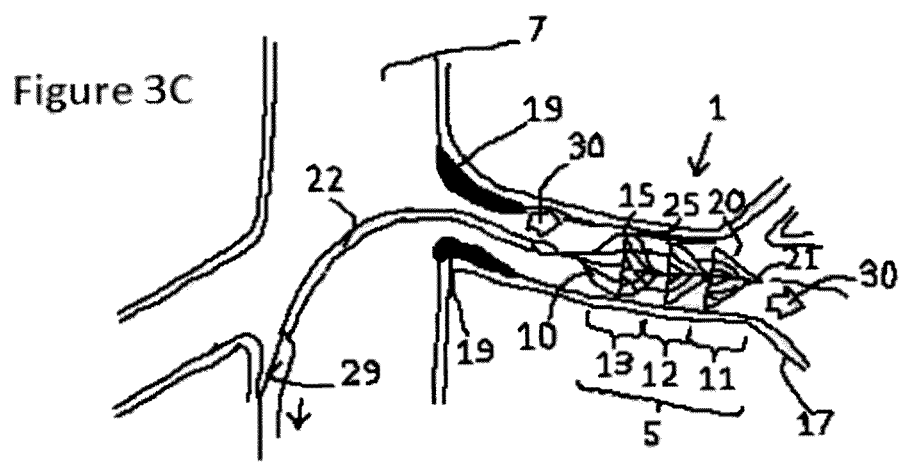
FIG. 3C is a cross-sectional, longitudinal view of the body vessel of FIG. 3B in which a stent is fully deployed.

Referring now to FIG. 3B, during the deployment of the filter device assembly 1, the structure 5 begins to expand to its expanded state when the structure 5 emerges from the distal end of the delivery tube 29. As shown in FIG. 3C, the frame 10 of the structure 5 in its expanded state engages the inner wall 17 of the vessel 7, to anchor the filter device 1 at the location of deployment in the vessel 7, thereby, preventing the filter device 1 from being moved by the blood flowing 30 through the vessel 7 and to ensure that blood does not flow around the device 1 but rather through the filter members 15, 20, 25.

Figure 3D:
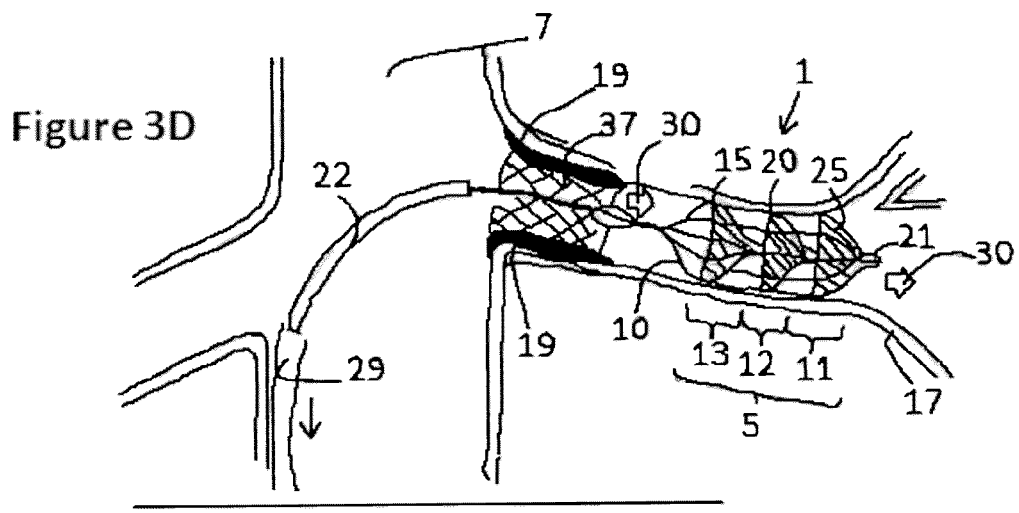
FIG. 3D is a cross sectional, longitudinal view of the body vessel of FIG. 3C in which treatment of the obstruction is being accomplished via the insertion of a stent according to one aspect of the present disclosure.
Figure 3E:
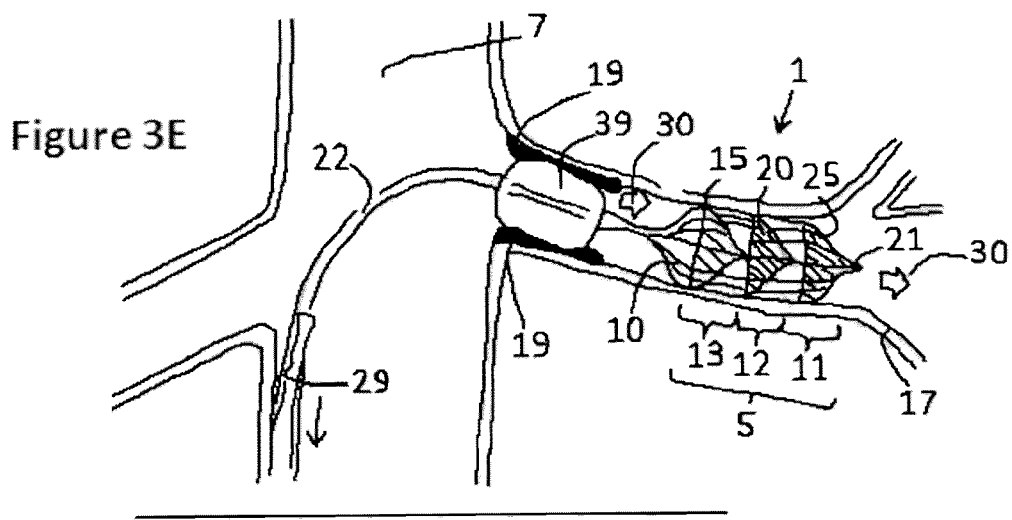
FIG. 3E is a cross-sectional, longitudinal view of the body vessel of FIG. 3C in which treatment of the obstruction is being accomplished via the insertion of a balloon according to another aspect of the present disclosure.

Referring now to FIGS. 3D and 3E, after the filter device assembly 1 is deployed, either a bare metal or drug eluting stent 37 (FIG. 3D) in an endovascular stenting procedure, a balloon 39 (FIG. 3E) during an angioplasty procedure, or another medical device may be deployed at the obstruction 19. The stent 37 or balloon 39 may expand as shown in FIGS. 3D and 3E to interact with the obstruction 19 and to maintain the flow of blood 30 through the obstructed area 19. One skilled in the art will understand that other types of treatments may be used to reduce or remove the obstruction, such as the use of lysins for chemical dissolution, mechanical thrombolysis, or the like, without exceeding the scope of this disclosure. The flow of blood through the filter device assembly 1 is maximized by the different porosity associated with the filter members 15, 25, and 20.

Referring now to FIG. 3C, the greater porosity of the first filter member 15 traps larger particulates or clots arising from the obstruction 19 and/or interaction of the stent 23 with the obstruction 19. Particulates that have a diameter smaller than the diameter of the orifices in the first filter member 15 that define the porosity ($P_1$) of the member 15 are allowed to pass through the member 15 along with the flow of blood to the adjacent filter member 25. Some of the particulates that pass through the first filter member 15 will become trapped in the adjacent filter member 25. Similarly, particulates that exhibit a diameter smaller than the diameter of the orifices or porosity ($P_2$) present in the second filter member 25 will pass through the second filter member 25 along with the flow of blood. Each additional filter member allows emboli having a diameter larger than the corresponding porosity, $[P_3 \ldots P_{(2+N)}]$, to be captured and emboli having a diameter smaller than the corresponding porosity, $[P_3 \ldots P_{(2+N)}]$, to pass there through along with the flow of blood to the adjacent filter member. Any particles that are small enough to pass through the second filter member 25 will not cause any detrimental effect on the health of the patient.

Figure 3F:
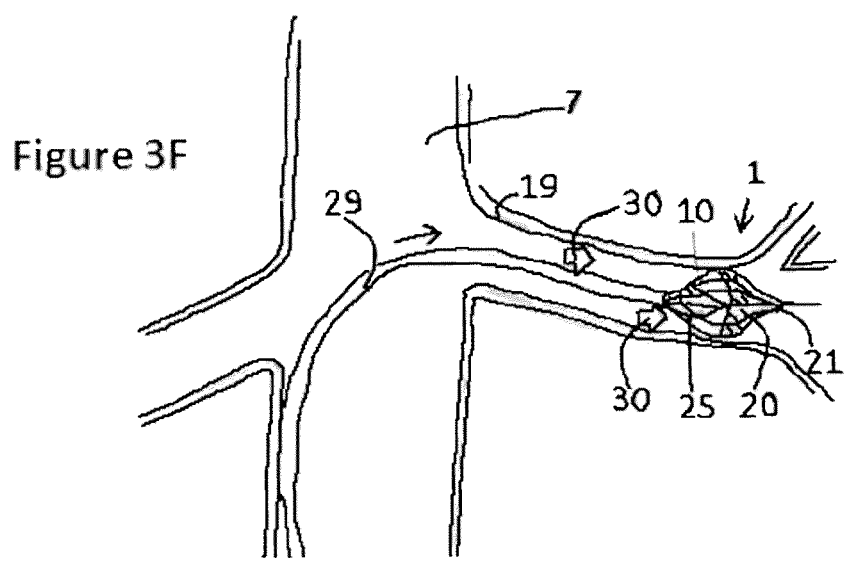
FIG. 3F is a cross-sectional, longitudinal view of the body vessel of FIG. 3C in which the multi-layer filter device assembly is withdrawn after the treatment of the obstruction according to yet another aspect of the present disclosure.

Referring now to FIG. 3F, upon completion of the treatment of the obstruction 19, the filter device assembly 1 may be removed from the artery or body vessel 7. In this operation, the filter device assembly 1 is allowed to transition from its expanded state to its collapsed state. The guide wire upon being coupled to the proximal end of the frame 10 (if not already coupled thereto) can pull the collapsed device assembly 1 into the catheter 29, wherein the device 1 and subsequently the catheter 29 may be removed from the body vessel 7.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A filter device assembly for capturing embolic particles in a blood flow in a body vessel, the device comprising:
   a structure having a frame with a predetermined shape, and a distal and proximal portion; the frame being configured to move between an expanded state for engagement with the body vessel and a collapsed state for delivery and retrieval, the structure having frame struts extending from the proximal portion to the distal portion longitudinally along an outside diameter of the filter device assembly, the frame struts proximally merging in the proximal portion toward a reduced diameter and configured to be coupled to a removal device; and
   at least a first filter member and a second filter member, the second filter member being arranged distally from the first filter member and configured to be placed downstream from the first filter member with respect to the blood flow, each filter member having a proximal part and a distal part, the proximal part circumferentially attached to the frame struts; the distal part of the first filter member closed such that the first filter member forms a first annulus chamber having porosity $P_1$ and the distal part of the second filter member closed such that the second filter member forms a second annulus chamber having porosity $P_2$;
   wherein the magnitude of the porosity for the first and second filter members follows the relationship $P_1 > P_2$;
   wherein the first and second filter members are configured in the expanded state to allow blood to flow there through and to capture emboli in the annulus chambers.

2. The filter device assembly of claim 1, wherein the porosity $P_1$ is at least about 150 micrometers and the porosity $P_2$ is equal to or less than about 50 micrometers.

3. The filter device assembly of claim 1, wherein the device assembly further comprises a middle portion, the middle portion arranged between the distal and proximal portions; and
   N additional filter members, wherein N is an integer greater than or equal to one; each of the N additional filter members being arranged distally from preceding filter members and having a proximal part and a distal part, the proximal part circumferentially attached to the middle portion of the frame; the distal part closed such that each N additional filter member forms an annulus chamber having a porosity $[P_3 \ldots P_{(2+N)}]$;
   wherein the magnitude of the porosity for each filter member follows the relationship $P_1 > [P_3 > \ldots > P_{(2+N)}] > P_2$.

4. The filter device assembly of claim 3, wherein the porosity of the first filter member, $P_1$, is at least about 150 micrometers, the porosity of the second filter member, $P_2$, is equal to or less than about 50 micrometers, and the porosity of each additional filter member, $[P_3 \ldots P_{(2+N)}]$, is greater than about 50 micrometers and less than about 150 micrometers.

5. The filter device assembly of claim 4, wherein each filter member comprises a material independently selected as one from the group of a non-woven material, a knit, a braid, a textile composite, a woven fabric, a molded polymer, a polymer film, or a combination thereof.

6. The filter device assembly of claim 3, wherein the distal part of each filter member is closed by being coupled to at least one of a shaft or an end hub.

7. The filter device assembly of claim 6, wherein the shaft includes perforated distal and proximal end sections; the proximal end section acting as struts to provide support for one filter member.

8. The filter device assembly of claim 1, wherein the structure in its expanded state has a substantially cylindrical shape.

9. The filter device assembly of claim 1, wherein the frame comprises one selected from the group of a metal, metal alloy, polymeric material, and combination thereof.

10. The filter device assembly of claim 1, wherein the proximal portion of the frame engages a guide wire for use in deployment and retrieval of the filter device assembly from the body vessel.

* * * * *